(12) United States Patent
Hansen

(10) Patent No.: US 6,674,050 B2
(45) Date of Patent: Jan. 6, 2004

(54) METHOD AND AN APPARATUS FOR CHARGING A HEATING CUSHION/WASHER

(76) Inventor: Knut Magne Hansen, Kaigaten 1, Haugesund (NO), 5527

( * ) Notice: Subject to any disclaimer, the term of this patent is extended or adjusted under 35 U.S.C. 154(b) by 0 days.

(21) Appl. No.: 10/203,958
(22) PCT Filed: Feb. 14, 2001
(86) PCT No.: PCT/NO01/00050
§ 371 (c)(1), (2), (4) Date: Aug. 13, 2002
(87) PCT Pub. No.: WO01/60307
PCT Pub. Date: Aug. 23, 2001

(65) Prior Publication Data
US 2003/0010482 A1 Jan. 16, 2003

(30) Foreign Application Priority Data
Feb. 16, 2000 (NO) .......................... 20000760

(51) Int. Cl.[7] .............................. A61F 7/02; F27D 11/00
(52) U.S. Cl. ................. 219/439; 219/385; 219/386; 219/401; 219/428; 222/146.5
(58) Field of Search ................. 219/439, 385, 219/386, 401, 428, 521; 222/146.5

(56) References Cited

U.S. PATENT DOCUMENTS

| | | | |
|---|---|---|---|
| 2,093,648 A | * | 9/1937 | Rice ..................... 219/401 |
| 4,077,390 A | | 3/1978 | Stanley et al. |
| 4,419,568 A | * | 12/1983 | Van Overloop ............ 219/441 |
| 5,058,563 A | | 10/1991 | Manker |
| 5,977,520 A | | 11/1999 | Madson, Jr. et al. |
| 6,018,145 A | * | 1/2000 | Moreno ..................... 219/401 |
| 6,259,067 B1 | * | 7/2001 | Faries, Jr. et al. ......... 219/428 |
| 6,265,695 B1 | * | 7/2001 | Liebermann ................ 219/385 |
| 6,316,750 B1 | * | 11/2001 | Levin ........................ 219/438 |

FOREIGN PATENT DOCUMENTS

| | | |
|---|---|---|
| DE | 3804304 | 8/1989 |
| SE | 467138 | 6/1992 |

* cited by examiner

Primary Examiner—Joseph Pelham
(74) Attorney, Agent, or Firm—Akerman Senterfitt, P.A.

(57) ABSTRACT

A method and an apparatus for charging a so-called heating washer (heating cushion) (10) with heat energy to be liberated at a chosen point of time through activating the heating washer (10) when the same e.g. has been placed on stiff/tender musculature. According to the invention, the heating washer is steamed, either one or more at a time, in a steam chamber positioned above a water chamber in a steam cooking apparatus (30), wherein the water chamber is separated from the overlying steam chamber by means of a horizontally directed partition plate (34), fluid communication being maintained between the chambers. The charging of the heating washer (10) by means of steam prevents that the heating washers are damaged in the way that may happen when boiled in water.

9 Claims, 11 Drawing Sheets

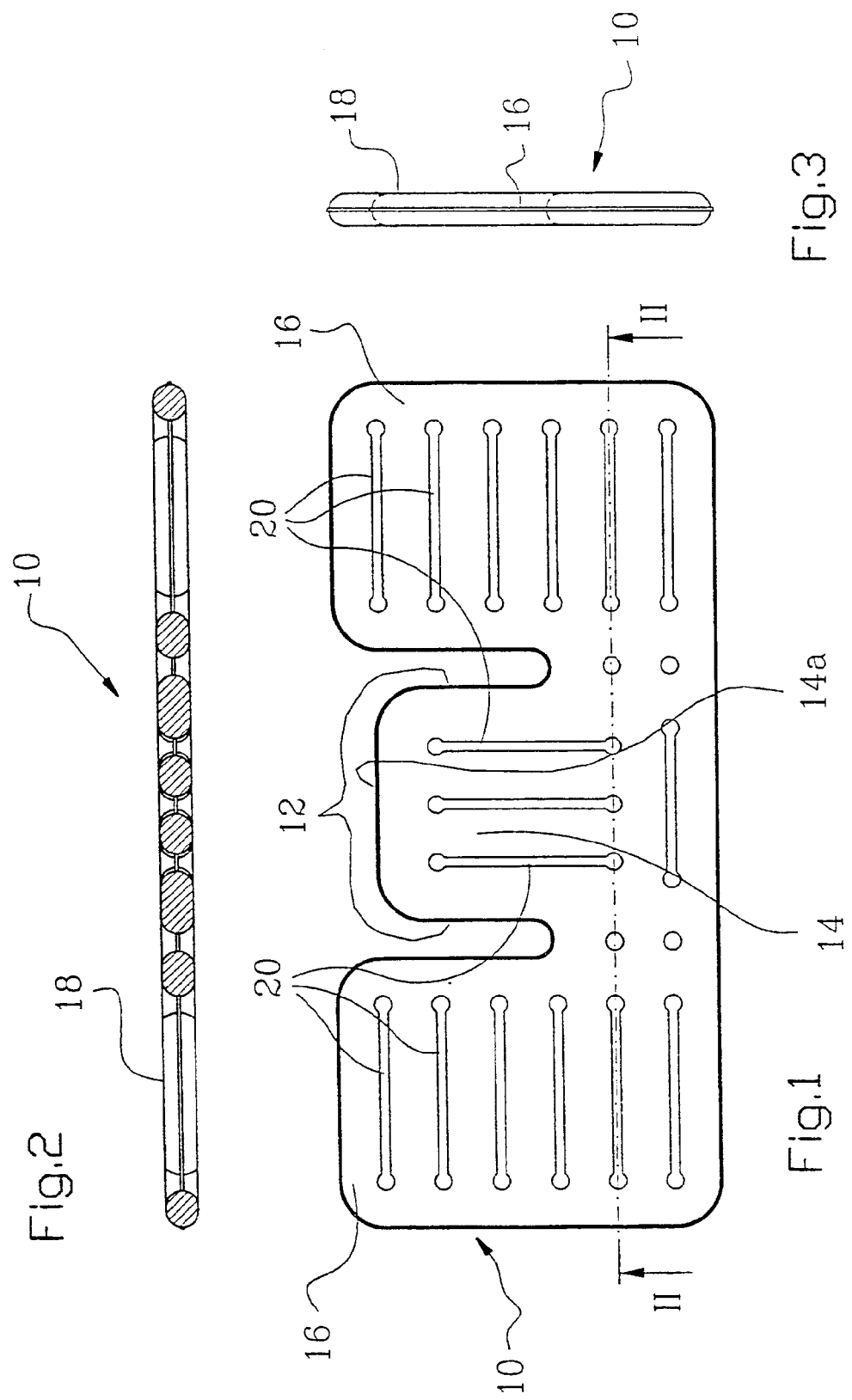

METHOD AND AN APPARATUS FOR CHARGING A HEATING CUSHION/WASHER

The present invention relates to a method for charging a heating cushion, often called a heating washer, with heat energy which can be liberated when needed through the activation of the heating washer when it is in position e.g. on the shoulders, simultaneously covering the nape of the neck upon the occurrence of stiff musculature in the shoulder/nape regions, and wherein one, in other respects, proceeds in accordance with the operational steps as defined in the preamble of claim 1.

Likewise, the invention relates to an apparatus for charging heating cushions/washers of the kind concerned, wherein the working operations are carried out by simple, suitable means.

Heating washers of the kind concerned are used within health care and nursing, for the prevention of overload torments and sufferings in working life, sports and leisure activities. Heating washers of this kind give relaxation, limbering-up, etc., as well as prevent sports damages. E.g. physiotherapists have for many years successfully used heating washers for these purposes.

One usual heating washer design comprises a relatively flat cushion/plate having two parallel, slot-shaped cavities partially separating the nape panel of the cushion/plate from the shoulder panel thereof. In this embodiment, the cushion/plate may have an elongate rectangular circumferential shape—except from in the nape panel portion where the circumferential shape extends irregularly because of the cavities—and the nape panel will then have a free circumferential edge and, moreover, be defined by the adjacent edges of the two parallel, slot-shaped cavities. Thus, the nape panel coheres with the remaining cushion/plate body along an imagined folding line extending parallelly with the complete longitudinal side of the rectangle.

Such heating washers each consists of an outer bag-shaped weldable plastic cover, the opposite side walls thereof being welded together locally, i.e. along narrow strip-shaped panels distributed across the surface area of the heating washer; in this embodiment, the weld strips in the name panel may extend perpendicularly to the mutually parallel weld strips within the remaining surface area of the heating washer. By means of the relatively densely positioned weld strips, the plastic cover is kept together upon filling and will not bulge unsuitably outwardly.

As chargeable, heat accumulating, upon activation heat liberating filler in the plastic cover, sodium acetate has been found to be well suitable. Likewise, it exhibits the advantageous property that it, encased within the plastic cover, may be shaped complementarily to the part of the body desired to be heated by means of the heating washer.

In accordance with prior art technique, such heating washers are, when they have given off the heat energy supplied thereto and, thus, are uncharged, recharged by being cooked in a charging apparatus, so that they are made ready for reuse. Prior art charging technique consists in boiling/heating the heating washer in water in a pot or other cooking vessel. The heating washer can be protected against scorching by means of a towel or other piece of cloth wrapped around the heating washer.

When the heating washer is boiled or heated in the water, the heating washer is capable of storing the heat energy supplied thereto, until it at a later point of time is activated for releasing the supplied, stored heat energy. A hitherto usual way of releasing the heating washer has been to use a thin piece of metal, and the heating washer can give off its heat whenever this is desirable to the user. Thus, the heat liberation may, of course, take place on any location whatsoever, irrespective of the availability of a heating source or not. A need for a heating source is only present when the heating washer is to be charged by heating/boiling. Heating washers are charged by placing them in hot water for about 20 minutes.

Heating washers of the kind concerned have a relatively large surface area, and the disadvantage or prior art charging technique through boiling/heating in a pot is that the same has to be rather voluminous. Alternatively, the heating washer has to be folded together, but this makes the charging process difficult. The known solution concerning charging heating washers with heat energy is rather cumbersome and circumstantial. Moreover, the pot may boil dry or the water therein boil too long. In both cases, the heating washer may be cooked into pieces. The heating washer may also be damaged if it rests too long in the boiling water after the boiling/heating is finished.

The object of the present invention has been to indicate a method for charging heating washers of the kind concerned wherein deficiencies, disadvantages and restrictions of use adhering to conventional and other known technique are eliminated or at least substantially reduced. Likewise, it is an object of the present invention to provide a charging apparatus for implementing this method and allow charging of a plurality of large heating washers at the same time.

The first of these objects is, according to the invention, realized by proceeding as set forth in accordance with the characterizing clause of claim 1 defining the method. The second object is achieved by means of a charging apparatus, the advantageous constructive features thereof being defined in the characterizing clause of the following, independent claim 2.

The essential operational step in the charging of the heating washer(s) with heat energy to be accumulated and stored until it is desired to have the heating washer released/activated in known manner for liberating the heat energy, comprises steam cooking/steaming, which gives an advantageous charging of the heating washers, simultaneously as the previous problems of dry boiling in the pot and a too long stay in the water now are eliminated. This involves a prolonged useful life of the heating washers.

The charging apparatus according to the invention is a special steam cooking apparatus adapted with a view of charging a plurality of relatively large washers in each charging treatment. There will exist a need for steam cooking apparatus of several orders, e.g. for firms/offices, and for private households, and these two main types of steam cooking apparatus will house a mutually differing number of heating washers.

Examples of preferred embodiments are further explained in the following, reference being made to the attached drawings which also illustrate a very much used heating washer (nap and shoulder heating washer) in its individual details, and wherein:

FIG. 1 shows a top/bottom plan view of a heating washer in the form of a shaped piece of material consisting of a plastic cover filled with sodium acetate;

FIG. 2 shows a section at line II—II in FIG. 1;

FIG. 3 shows an end view of the heating washer according to FIG. 1;

Figure 4:
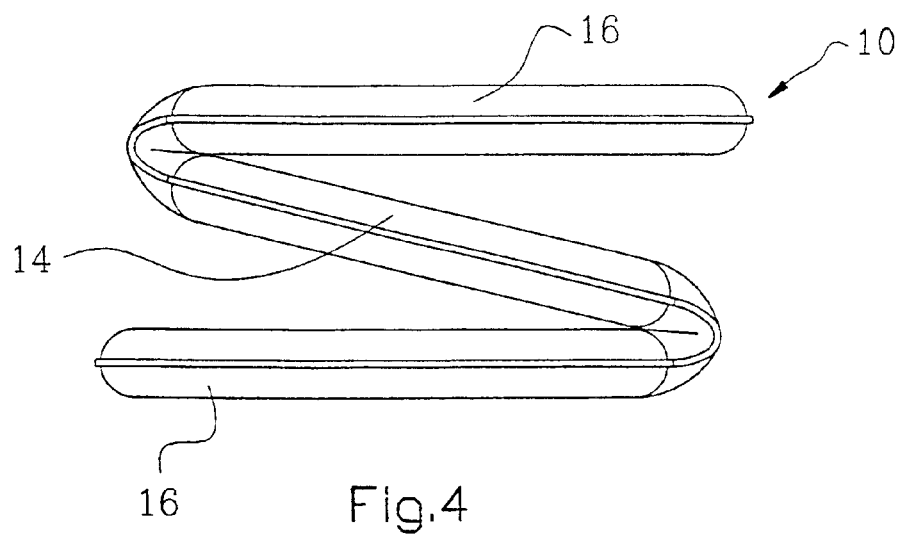
FIG. 4 shows the same type of view as in FIG. 3, but here the three panels of the heating washer are placed in a S-shape in relation to each other, said S-shape being advantageous for its retaining in a specially shaped and designed steam cooking apparatus during charging.
Figure 12:
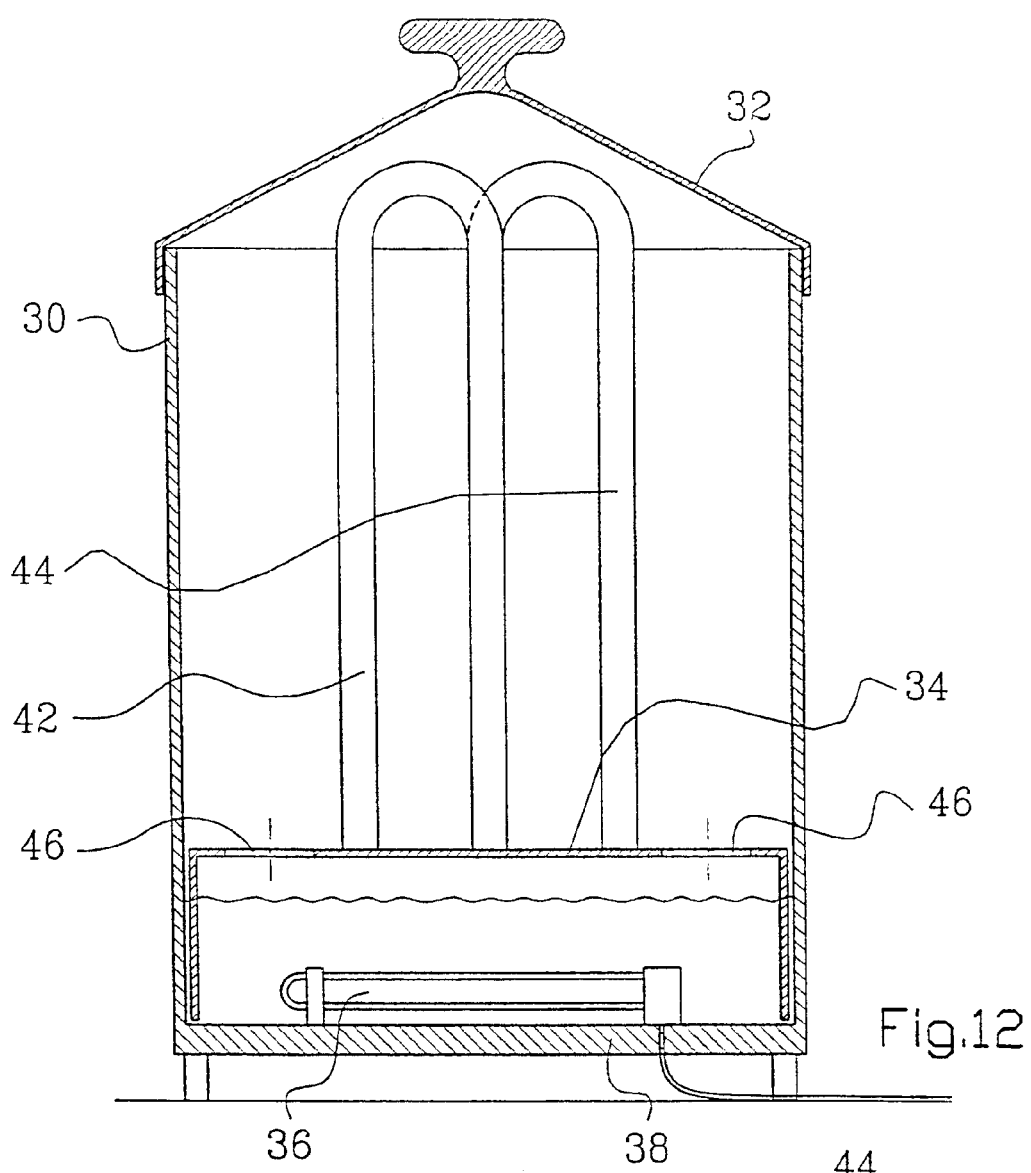
FIGS. 12–16 show a steam cooking apparatus of another embodiment, internally equipped, shaped, designed and dimensioned for charging/steaming one heating washer, FIG. 12 showing a vertical longitudinal view of this steam cooking apparatus design.
Figure 13:
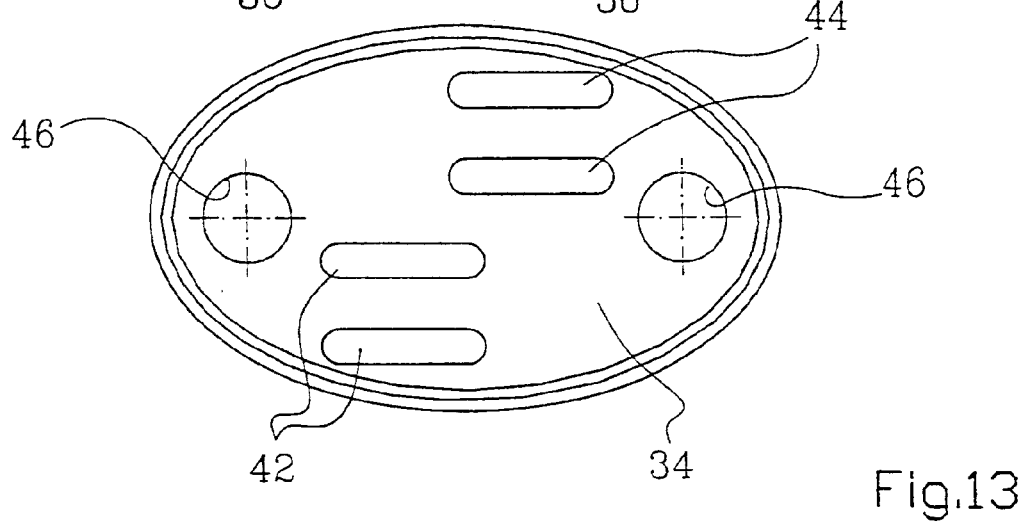
Figure 14:
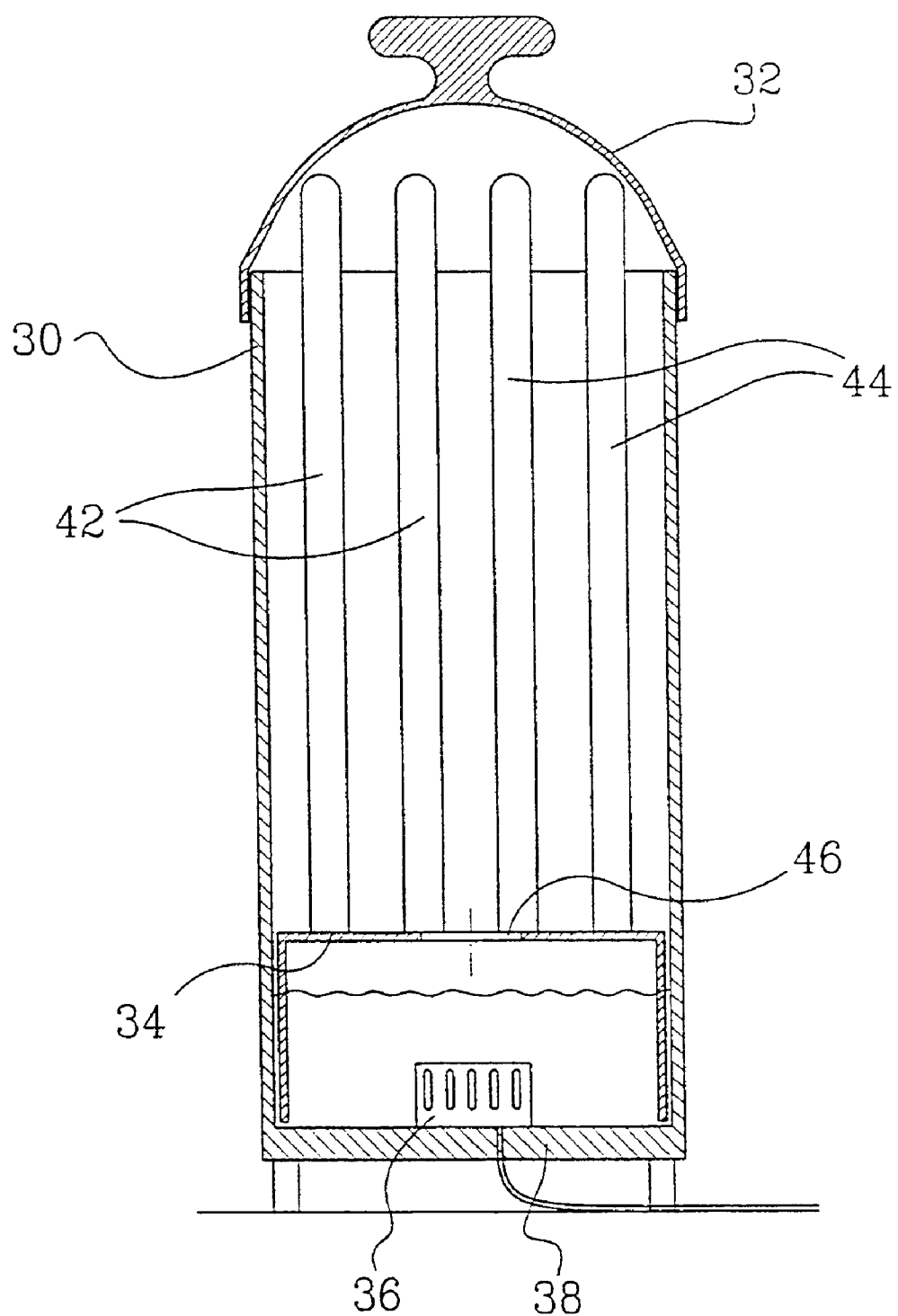
Figure 15:
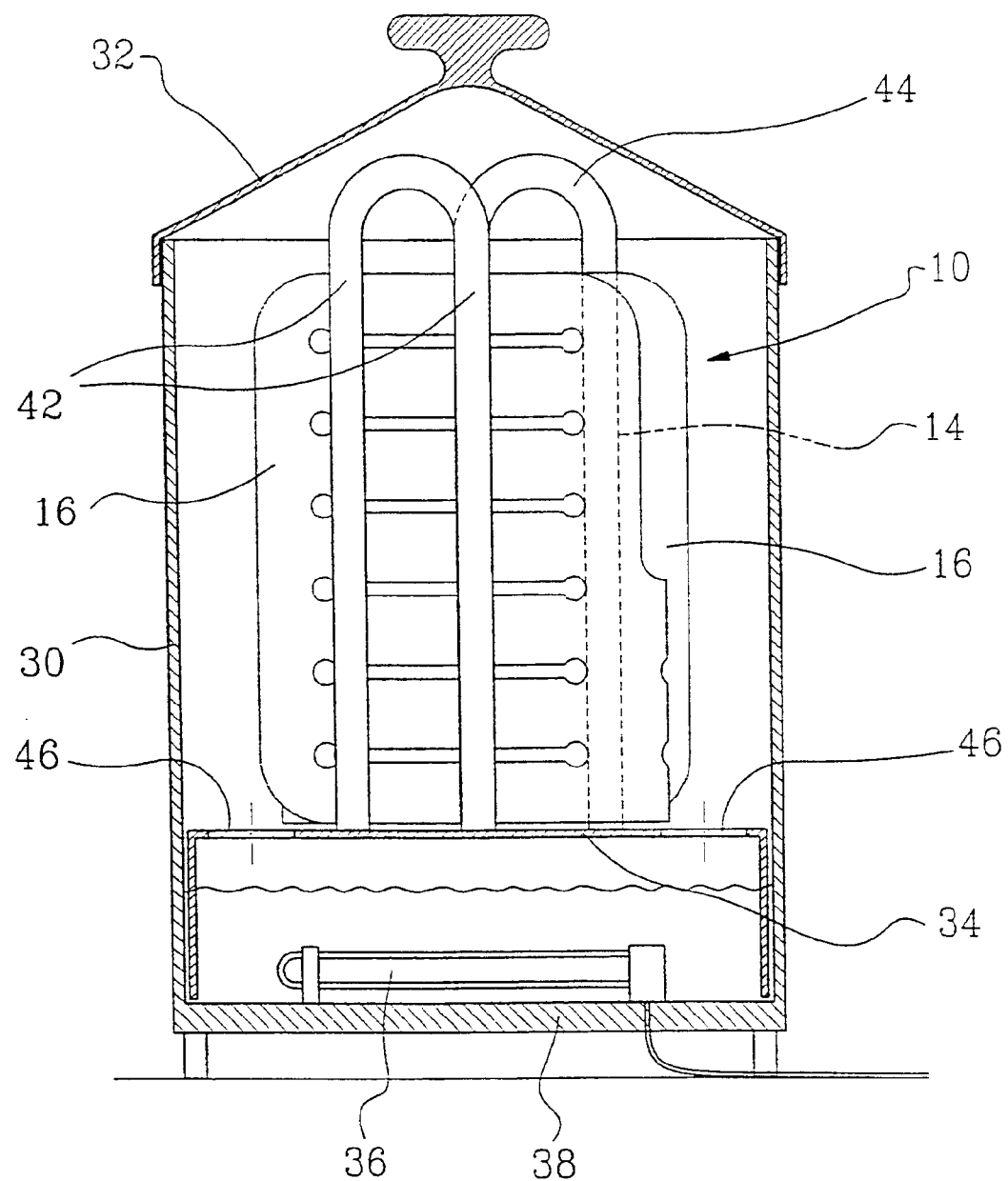
Figure 16:
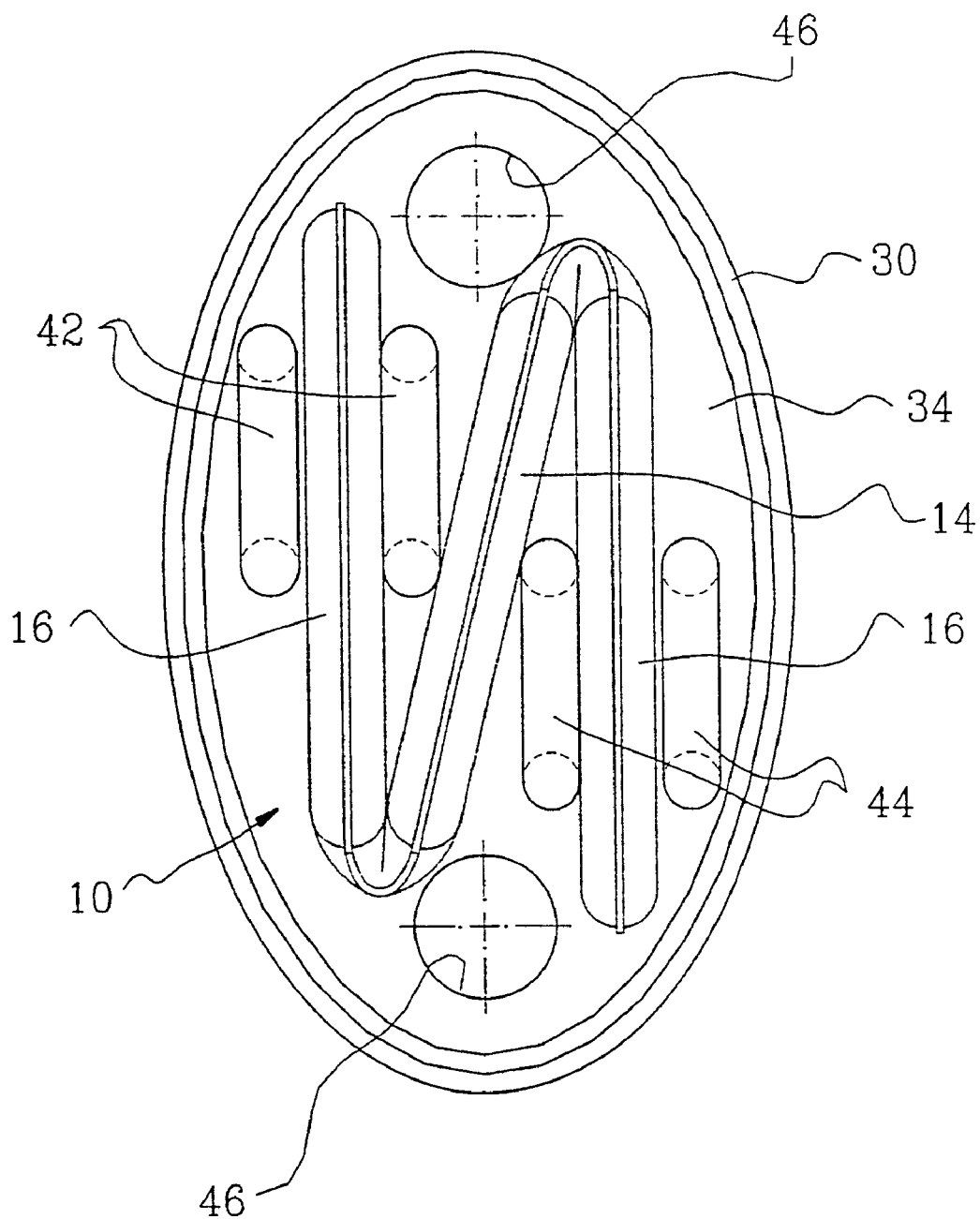

FIG. 13 showing a lateral horizontal section of the steam cooking apparatus according to FIG. 12, wherein the container wall circumference substantially follows an ellipse;

FIG. 14 shows a vertical section placed parallel to the small axis of the ellipse;

FIG. 15 corresponds to FIG. 12, but here a heating washer in completely expanded condition has been threaded into the retaining device;

FIG. 16 shows, on a larger scale, a lateral horizontal section through the steam cooking apparatus shown in FIG. 15, with an inserted, partially folded heating washer according to FIG. 4 placed in a particular way in two upright holding bows of the retaining device.

Reference is first made to FIGS. 1–5 of the drawings in order to describe the shape, design, dimensions and construction of a typical heating washer. The heating washer which as such is generally denoted at 10, has a flat, see FIGS. 2 and 3, substantially rectangular circumferential shape, but two parallel, mirror-symmetrical cavities 12 define a central panel 14 having a withdrawn edge 14a from the side panels 16 of the heating washer.

The heating washer 10 comprises an external closed cover 18, the upper and lower wall thereof being welded together at strip-like welding panels 20 distributed across the surface area of the heating washer 10 and, within the side panels 16, extend in the longitudinal direction of the heating washer, while the welding panels 20 substantially across the central panel 14 extend in the lateral direction of the heating washer 10, perpendicularly to the longitudinal welding panels 20.

Within the closed plastic foil cover 18 is, prior to the closure, placed e.g. sodium acetate, an in per se known material well suited for the purpose capable of accommodating and storing supplied heat energy, until there exists a need for the heat energy. The heating washer is activated (by means of a piece of metal) for release and liberation of the heat energy supplied thereto. The circumferential shape of the heating washer 10 shown is particularly adapted for heating and accompanying softening-up nap/shoulder musculature. The construction and choice of materials, uses as well as properties are all known factors and are, therefore, not described further here.

During the bending and shaping complementarily to the shape of its place of placing on the body; in the present case in the regions of nap/shoulders, the free portions of the side panels 16 each being bent over a shoulder, while the central panel 14 is bent upwardly and shaped substantially according to the nap of the neck.

Figure 5:
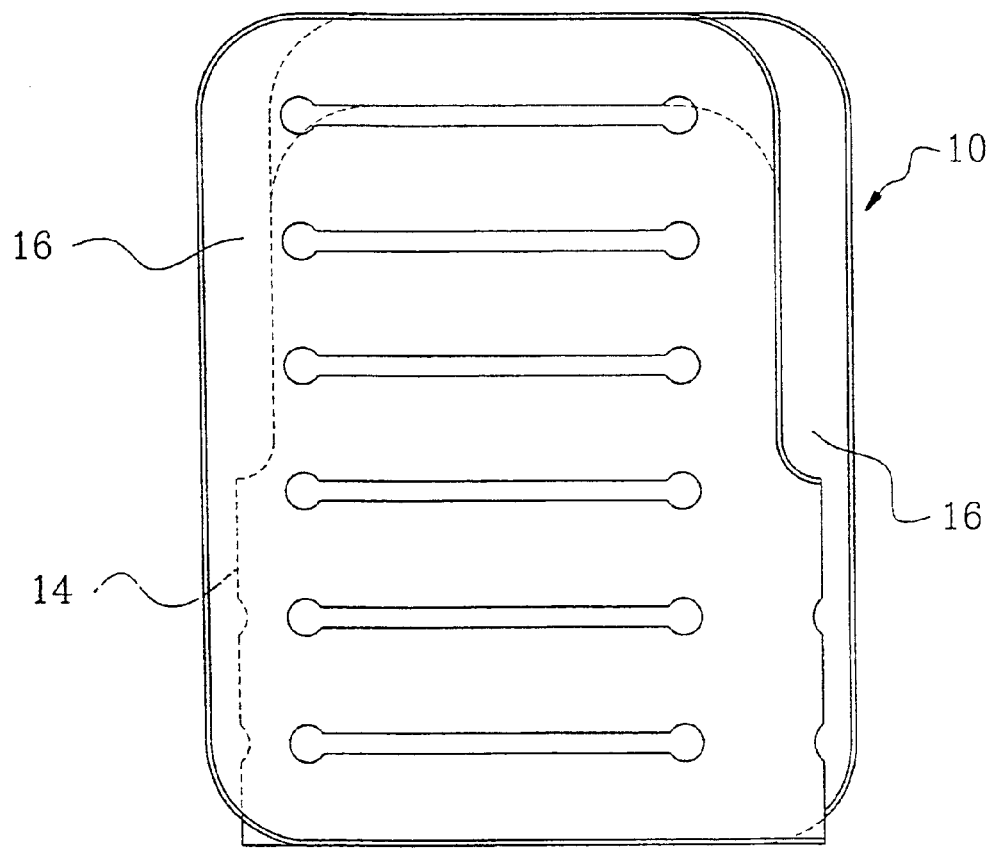
FIG. 5 shows the heating washer bent in shape in the same manner as in FIG. 4, but as seen towards one of the main faces of the panels.

However, FIGS. 4 and 5 show a heating washer bent into some kind of S-shape in a charging position, confer FIG. 13, wherein a heating washer in this S-bent shape is retained during the heating through steam cooking/steaming.

Figure 6:
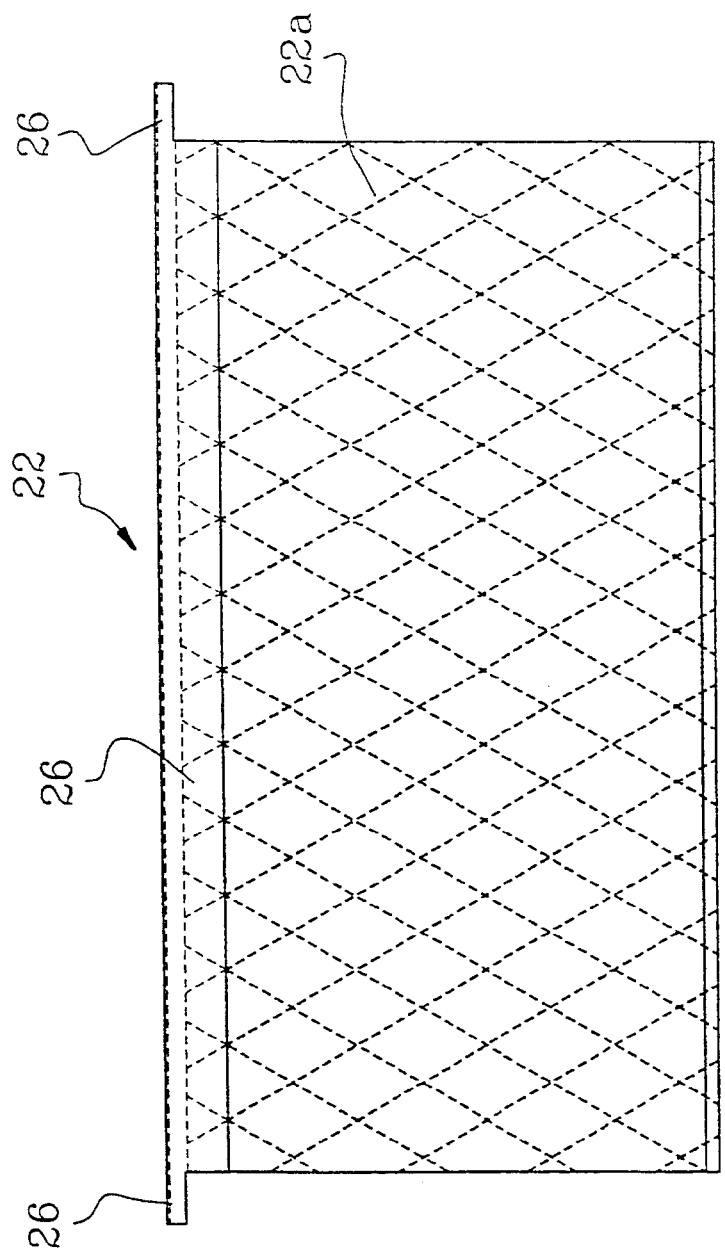
FIG. 6 shows a side elevational view of a steam permeable suspension pocket ("filing jacket") for the accommodation of a plurality of large heating washers parallel side by side.
Figure 7:
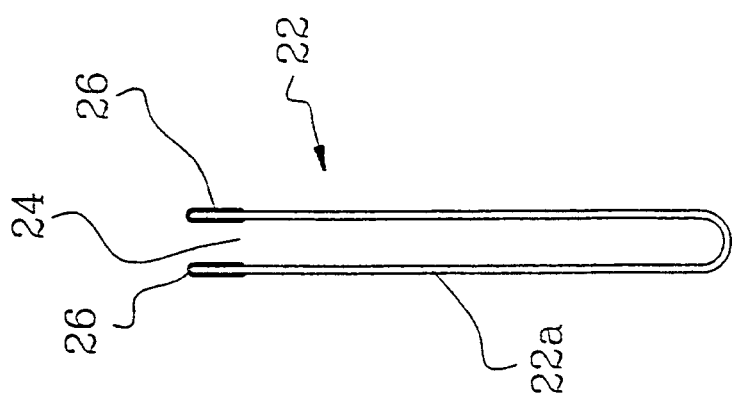
FIG. 7 shows such a suspension pocket in end view/cross section.

For charging more heating washers 10 than one or a couple of them through steam cooking/steaming, a kind of suspension pockets have been developed in accordance with the invention, generally denoted at 22, see FIGS. 6 and 7. The suspension pockets 22 each has a long, narrow U-shaped circumference in cross section, provided with an upright insertion and outlet opening 24 defined by bracing and suspension rails 26 projecting outside the pocket proper at each end. These projecting portions 28 form suspension means for placing on a container's 30 upper edge face, see FIG. 11, and enable, subsequently to terminated charging of a number of heating washers, a particularly simple withdrawal of the heating washers or the suspension pockets 22 having the charged heating washers 10 laying therein and which, according to FIG. 11, each lays in a suspension pocket of its own, in completely unfolded, plane condition.

Preferably, the wall 22a of the suspension pockets 22 is steam permeable. In some cases, an amount of steam supplied from above through the upper U-opening maybe sufficient for charging the heating washer.

Now, reference is made to FIGS. 8–11, for the description of a first embodiment of the steam cooking apparatus, in which a plurality of heating washers simultaneously can be charged, preferably in suspension pockets according to FIGS. 6 and 7.

In accordance with the invention, a charging apparatus for heating washers comprises a rectangular steam cooking apparatus, the container wall thereof, as mentioned, is denoted at reference numeral 30. The container 30 of the steam cooking apparatus has a steam hood 32 and a, possibly steam permeable/perforated, partition plate 34 dividing the container 30 into a (a) lower water-filled part wherein cooking/boiling and steam development is initiated by means of an imerged electrical heating element 36 resting on the container bottom wall's 38 upper face and (b) an overlying steam-filled part wherein the heating washers will be placed/suspended during charging.

Figure 8:
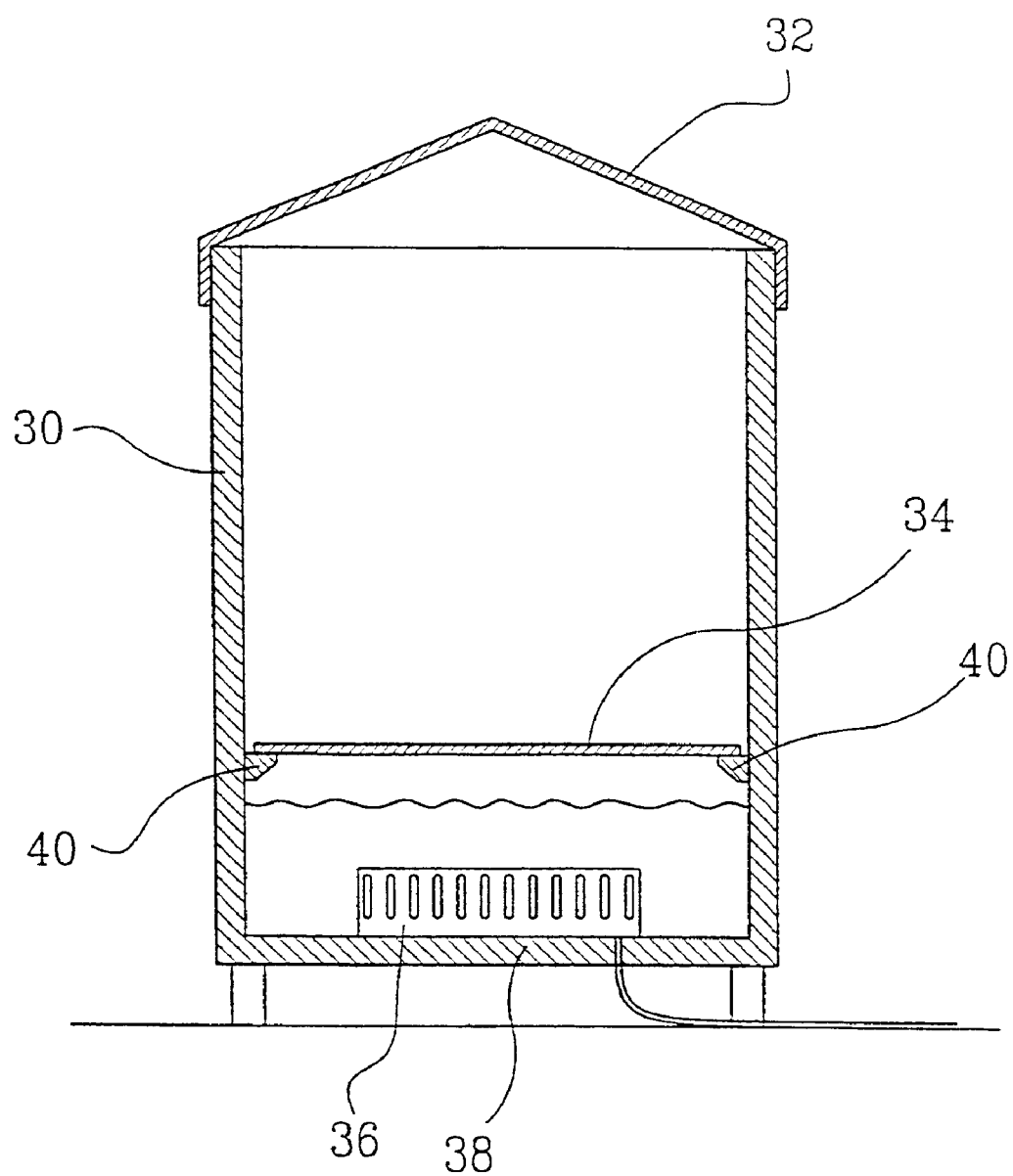
FIG. 8 shows a steam cooking apparatus for heating washers in a vertical section parallel to the short sides.
Figure 9:
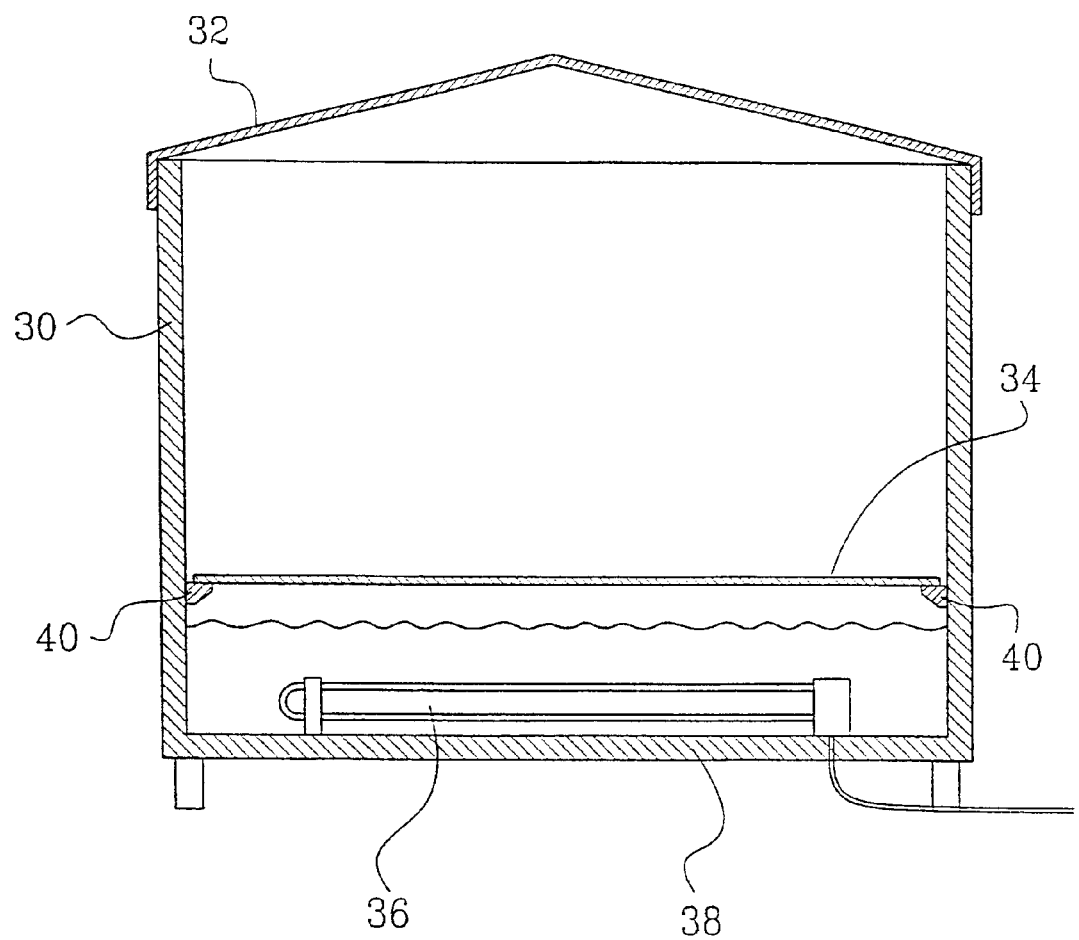
FIG. 9 shows the same steam cooking apparatus as in FIG. 8, but seen in a longitudinal vertical section.

The horizontally disposed partition plate 34 has a longitudinal and a lateral dimension which in both cases are smaller than the container's 30 corresponding internal dimensions in the horizontal plane and rests on small brackets 40 distributed with equal spacings along both longitudinal sides and both short sides as well as being attached to opposing inner sides of the container 30, projecting inwardly into the same, see especially FIGS. 8 and 9.

Thus, along the internal container wall, between the brackets 40 and between the inner wall and outer partition plate edges, narrow vertically through-going slots are formed, through which water steam may ascend from the underlying, water-filled container member during the boiling of the water.

Figure 10:
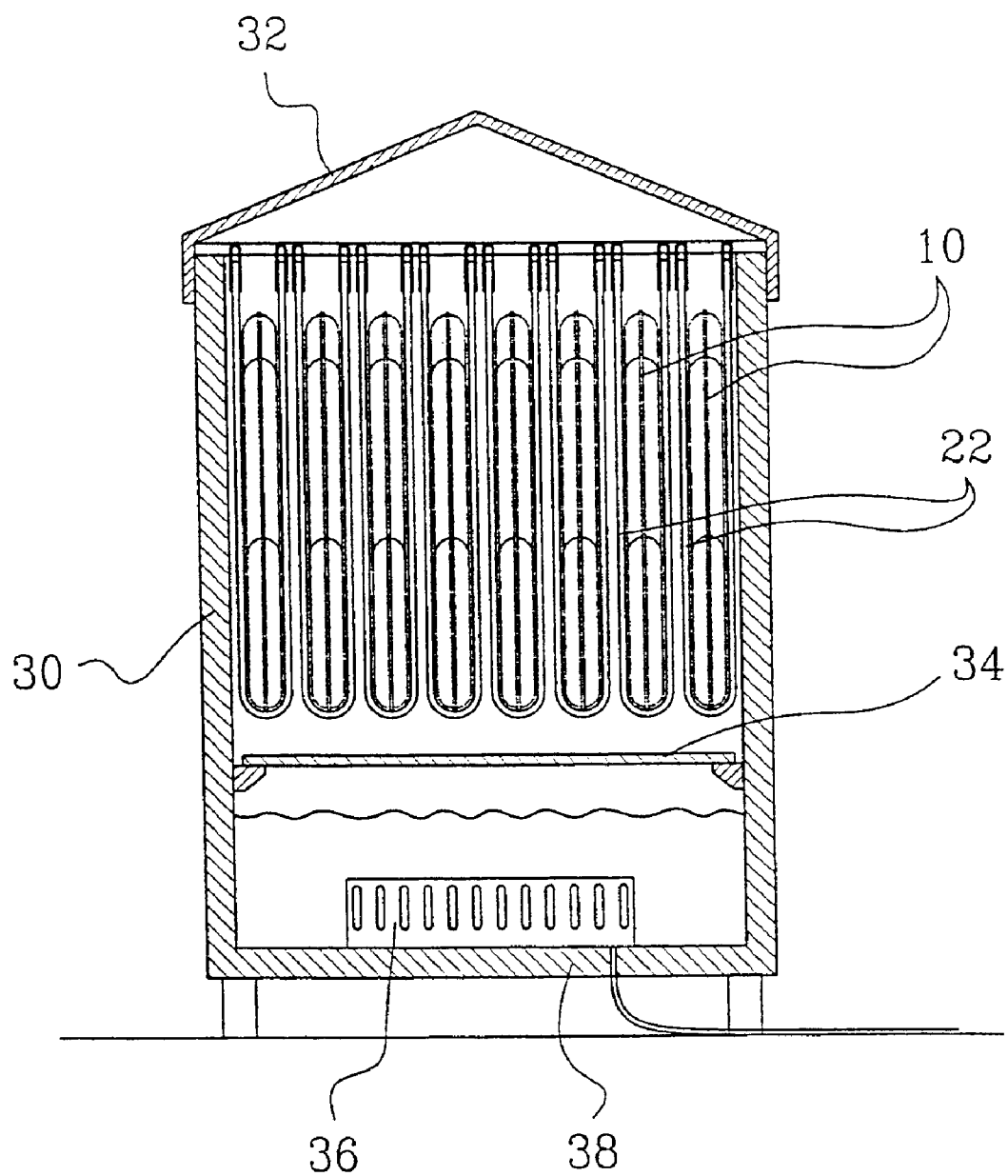
FIG. 10 shows the steam cooking apparatus in the same section as in FIG. 8, but comprising eight suspended hanging pockets each containing a heating washer of the nap-shoulder-type.
Figure 11:
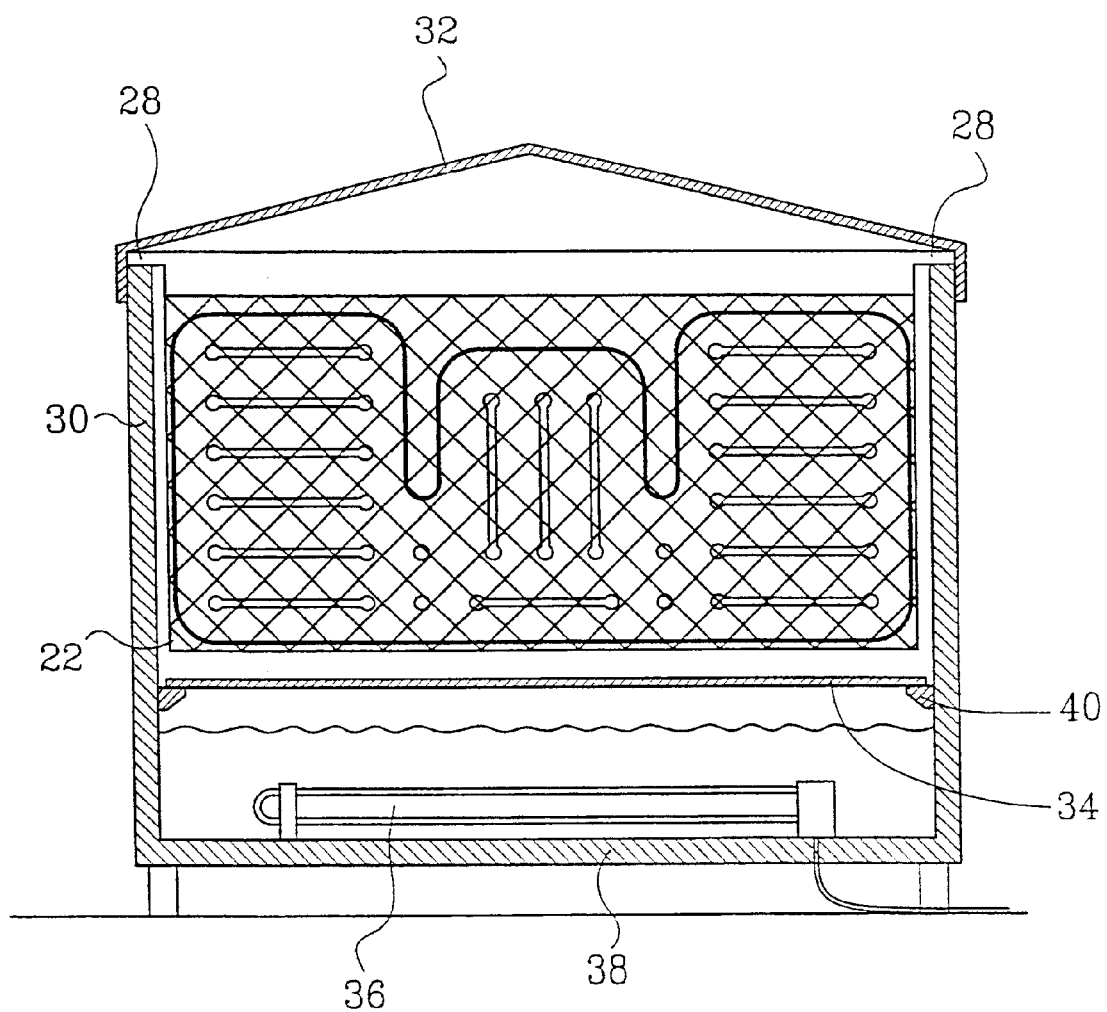
FIG. 11 shows the steam cooking apparatus according to FIGS. 8 and 9 in the same sectional view as in FIG. 9, but comprising suspended hanging pockets containing heating washers in completely expanded, plane condition according to FIG. 8.

Respectively, FIGS. 10 and 11 correspond to FIGS. 8 and 9, but in the first-mentioned figures, on the upper container edge of the steam cooking apparatus, bracing and suspension rails 26 are suspended, said rails belong to suspension pockets 22 of the kind shown in FIGS. 6 and 7, and wherein in each suspension pocket 22 is inserted a heating washer 10 according to FIGS. 1 and 3 in completely unfolded condition.

During the boiling of water in the lower container part of the steam cooking apparatus, water steam will be generated and ascend upwardly into the overlying charging container part wherein one, for the charging of the heating washers, operates with steam in lieu of boiling or heated water. The time of charging is about 20 minutes.

The charging/steam cooking apparatus according to FIGS. 8–11 has a relatively large capacity, as it does not presents problems to charge e.g. eight heating washers 10 at the same time.

FIGS. 12–16 show a charging apparatus in the form of a steam cooking apparatus for domestic use; shaped, designed and dimensioned for charging one single hating washer 10 at a time. This heating washer 10 is folded partially together along parallel, imaginary folding lines between the individual panels 16, 14, 16, see FIGS. 4 and 5, so that the steam cooking apparatus becomes particularly space-saving.

This steam cooking apparatus constituting a charging apparatus for heating washers for domestic use has, except from the retaining device for the heating washer 10, the same fundamental construction as the charging/steam cooking apparatus according to FIGS. 8–11. Therefore, the same reference numerals have been used for the same/similar parts in the two embodiments, respectively FIGS. 8–11 and FIGS. 12–16.

However, in the horizontal partition plate in the steam cooking apparatus according to FIGS. 12–16, two vertically through-going holes 46 have been formed, for steam transfer from the container's 30 water chamber below the partition plate to the overlying steam chamber constituting the charging chamber.

In accordance with FIGS. 12–16, in the charging/steam chamber, two upright holding bows 42 and 44 have been disposed. The pairs of holding bows 42, 42 and 44, 44 are displaced in relation to each other in a horizontal plane, see especially the sectional views according to FIGS. 13 and 16 (last-mentioned figure on a larger scale), where it appears that the container 30 for space-saving purposes is shaped with oval/elliptical circumferential form.

FIG. 16 shows in association with FIG. 15 how one heating washer 10 is threaded down onto the retaining device 42, 44, to be firmly kept within the steam chamber during the charging in completely expanded condition.

What is claimed is:

1. An apparatus for charging at least one heating washer intended to heat and soften-up stiff, tender musculature, the heating washers during charging being supplied with heat energy to be stored for subsequent liberation upon activation of the heating washer, comprising:
    a water chamber for boiling water by means of a heating element assigned thereto;
    a steam chamber constituting the charging chamber for the at least one heating washer, said steam chamber in fluid communication with the water chamber for the transfer of steam therefrom; and
    one or more parallel disposed suspension pockets hangable within the steam chamber,
    said suspension pockets formed for admission of a heating washer and steam supply to the internal cavities of the suspension pockets.

2. An apparatus as defined in claim 1, wherein the suspension pocket walls are steam permeable.

3. An apparatus as defined in claim 1, wherein the lower water and upper steam chambers are separated by a substantially horizontal partition plate, said partition plate through dimensioning and mounting or through perforations providing steam transfer from the water chamber to the steam chamber.

4. An apparatus as defined in claim 1, wherein an upright carrier is assigned to the steam chamber for stably but releasably retaining said heating washer folded partially together in S-form along two parallel folding lines defining a central panel from two outer panels cohering therewith.

5. An apparatus as defined in claim 4, wherein the upright carrier comprises eight members forming two holding members which are displaced in the longitudinal and lateral directions of the steam chamber, each holding member forming a vertical slot for the accommodation of one outer panel each, the spacing between the two closest members, one in each holding member insignificantly exceeding the thickness of the intermediate panel of the heating washer.

6. An apparatus as defined in claim 2, wherein the lower water and upper steam chambers are separated by a substantially horizontal partition plate, said partition plate through dimensioning and mounting or through perforations providing steam transfer from the water chamber to the steam chamber.

7. An apparatus as defined in claim 2, wherein an upright carrier is assigned to the steam chamber for stably but releasably retaining said heating washer folded partially together in S-form along two parallel folding lines defining a central panel from two outer panels cohering therewith.

8. An apparatus as defined in claim 3, wherein an upright carrier is assigned to the steam chamber for stably but releasably retaining said heating washer folded partially together in S-form along two parallel folding lines defining a central panel from two outer panels cohering therewith.

9. A method for charging at least one heating cushion washer, intended to heat and soften-up stiff, tender musculature, the heating washers during charging being supplied with heat energy to be stored for subsequent liberation upon activation of the heating washer, said heating washer being charged by means of a water chamber for boiling water including a heating element assigned thereto, comprising:
    charging the heating washer within a steam chamber in fluid communication with the water chamber for the transfer of steam therefrom, and while the at least one heating washer is suspended in one or a plurality of parallel disposed suspension pockets hung up within the steam chamber, said suspension pockets formed for admission of a heating washer and steam supply to the internal cavities of the suspension pockets.

* * * * *

UNITED STATES PATENT AND TRADEMARK OFFICE
CERTIFICATE OF CORRECTION

PATENT NO. : 6,674,050 B2
DATED : January 6, 2004
INVENTOR(S) : Knut Magne Hansen It is certified that error appears in the above-identified patent and that said Letters Patent is hereby corrected as shown below:

Column 1,
Line 42, replace "name" with -- nape --

Column 2,
Line 55, replace "nap" with -- nape --

Column 3,
Lines 16 and 66, replace "nap" with -- nape --

Column 4,
Lines 5 and 8, replace "nap" with -- nape --

Column 5,
Line 13, replace "presents" with -- present --
Line 17, replace "hating" with -- heating --

Signed and Sealed this

Twenty-first Day of June, 2005

JON W. DUDAS
*Director of the United States Patent and Trademark Office*